United States Patent [19]
Berg et al.

[11] 4,280,491
[45] Jul. 28, 1981

[54] POWERED AIR RESPIRATOR

[75] Inventors: Richard C. Berg, Bloomington; Emil J. Kvall, North St. Paul, both of Minn.

[73] Assignee: Minnesota Mining and Manufacturing Company, St. Paul, Minn.

[21] Appl. No.: 127,953

[22] Filed: Mar. 7, 1980

[51] Int. Cl.³ .............................................. A61F 9/06
[52] U.S. Cl. ......................... 128/201.24; 128/201.25; 2/171.3
[58] Field of Search ...................... 128/201.24, 201.25, 128/201.29, 201.23; 2/171.3

[56] References Cited

U.S. PATENT DOCUMENTS

| | | | |
|---|---|---|---|
| 3,223,086 | 12/1965 | Denton | 128/201.24 |
| 3,413,972 | 12/1968 | Depping | 128/201.23 |
| 3,736,927 | 6/1973 | Misaqi | 128/201.25 |
| 3,822,698 | 7/1974 | Guy | 128/201.25 |
| 3,963,021 | 6/1976 | Bancroft | 218/201.25 |
| 4,133,308 | 1/1979 | Lowe et al. | 128/201.25 |
| 4,136,688 | 1/1979 | Gorman | 128/201.25 |

FOREIGN PATENT DOCUMENTS 1426432 2/1976 United Kingdom .
2032284 5/1980 United Kingdom ................ 128/201.25

Primary Examiner—Henry J. Recla
Attorney, Agent, or Firm—Cruzan Alexander; Donald M. Sell; Edward T. Okubo

[57] ABSTRACT

A powered air respirator which provides hardhat (safety helmet), respiratory, eye and face protection and comprises a hardhat, a shell member spaced from and overlying the hardhat, air filtering means in the space between the shell member and the hardhat, a face shield assembly attached to and depending from the front of the shell member, a transparent face shield in said face shield assembly, face sealing means on the peripheral edge of said face shield assembly to seal against a user's face from temple to temple and an air circulating means located in the rear portion of the shell member is disclosed.

6 Claims, 2 Drawing Figures

POWERED AIR RESPIRATOR

BACKGROUND OF THE INVENTION

The present invention relates to respirators and more particularly to powered air respirators for use in dusty or debris laden atmospheres or, in atmospheres contaminated with toxic dusts, mists or fumes provided that suitable filter media are utilized.

Much effort has been expended in efforts to provide respiratory, eye and face protection to workers exposed to dust and debris in the atmosphere. Examples of such devices are disclosed in Depping U.S. Pat. No. 3,413,972, Guy U.S. Pat. No. 3,822,698, Bancroft U.S. Pat. No. 3,963,021, Lowe and Odell U.S. Pat. No. 4,133,308, and Gorman U.S. Pat. No. 4,136,688. However, each of these devices proved to be disadvantageous in one or more respects. Perhaps the major disadvantage of these prior art devices has been the gap between the user's chin and the lower edge of the visor found in Guy U.S. Pat. No. 3,822,698, Bancroft U.S. Pat. No. 3,963,021, Lowe et al. U.S. Pat. No. 4,133,308 and Gorman U.S. Pat. No. 4,136,688. While it has been suggested that the gap could be minimized or even eliminated if an exhaust valve were incorporated into the lower edge of the visor, it has been reported that even a small opening at the chin has permitted the intrusion of particles from grinding operations. It is expected that the exhaust valve, which would always be open under the operating pressures encountered, would itself be an opening through which particles from grinding operations could enter the visor. Devices which fully enclose the head and shoulders of a user are quite cumbersome to wear and restrict freedom of movement.

SUMMARY OF THE INVENTION

The present invention relates to a powered air respirator which provides hardhat (safety helmet), respiratory, eye and face protection and comprises a hardhat, a shell member spaced from and overlying the hardhat, air filtering means in the space between the shell member and the hardhat, a face shield assembly attached to and depending from the front of the shell member, a transparent face shield in said face shield assembly, face sealing means on the peripheral edge of said face shield assembly to seal against a user's face from temple to temple and an air circulating means located in the rear portion of the shell member. In use, the powered air respirator provides filtered ambient air in a stream over the user's face which exits at the temple.

DETAILED DESCRIPTION OF THE INVENTION

Figure 1:
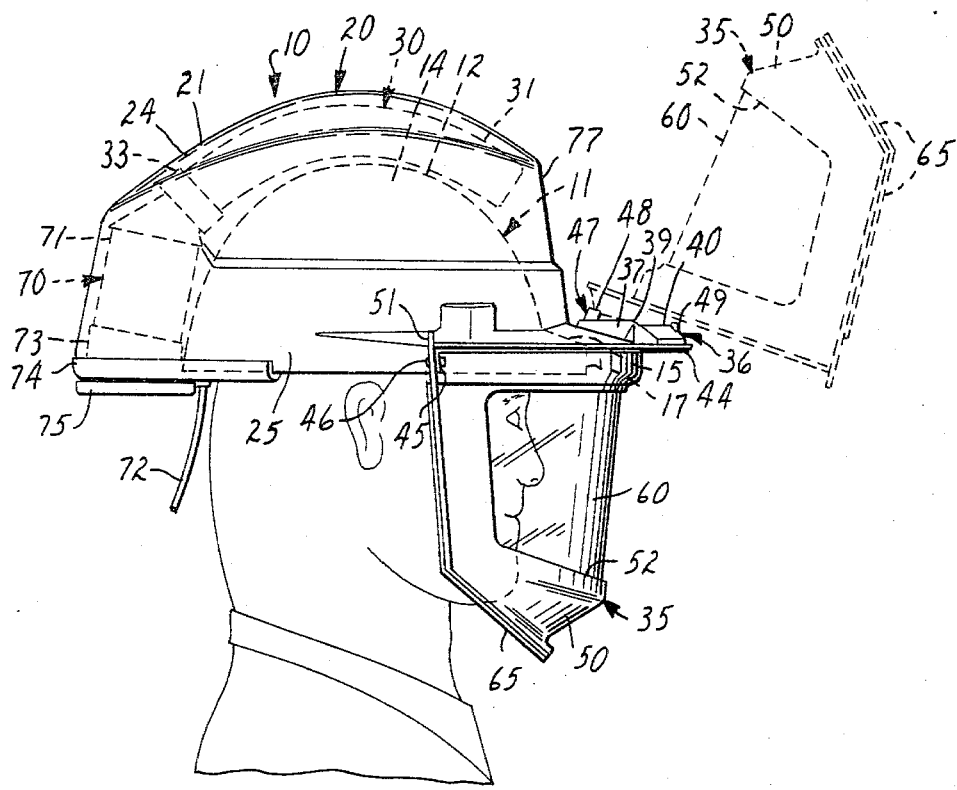
FIG. 1 is a side elevational view of the powered air respirator comprising the invention as worn and also shows the face shield assembly in a raised position in dotted lines.
Figure 2:
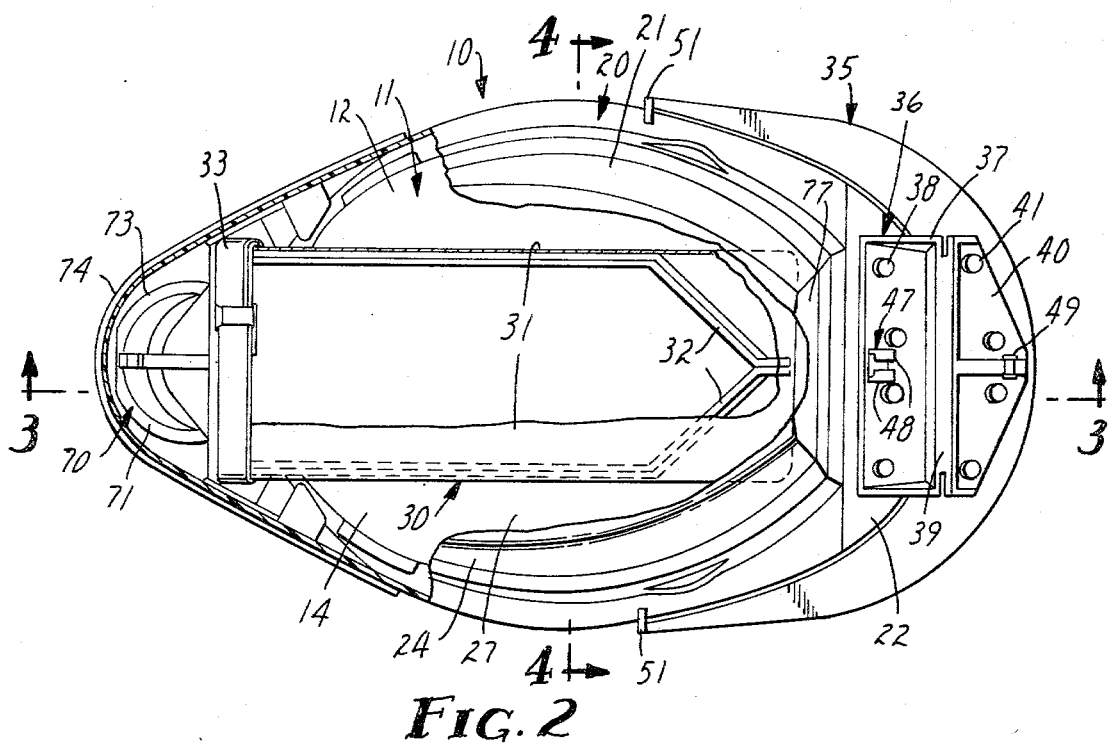
FIG. 2 is a top plan view, partly in section, of the powered air respirator of FIG. 1.
Figure 3:
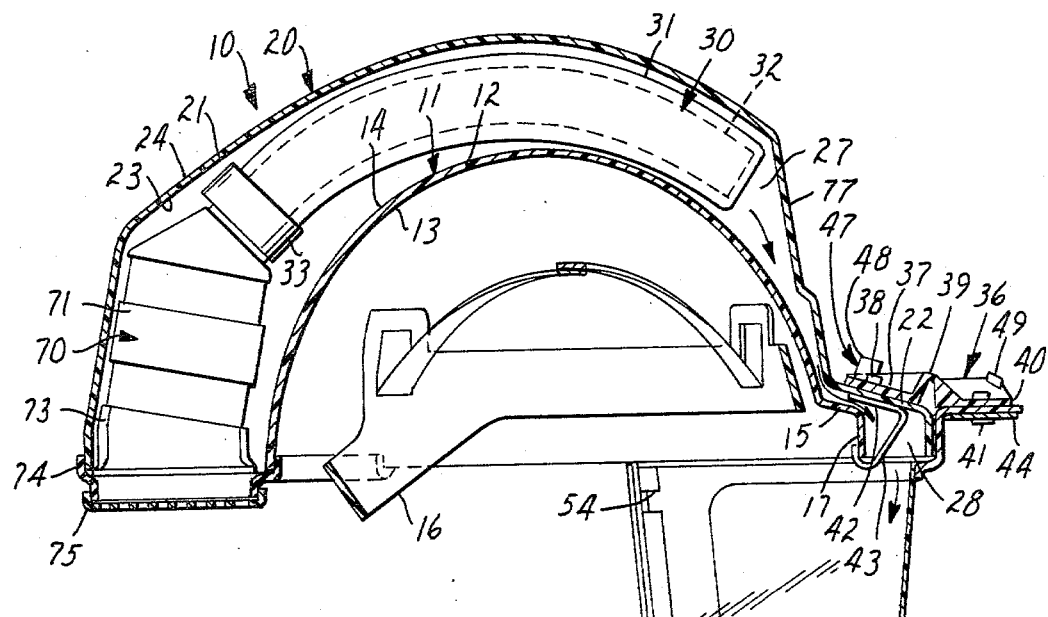
FIG. 3 is a sectional view along the line 3—3 of FIG. 2.

Referring to the drawings and particularly FIGS. 1 and 3, the powered air respirator 10 of the invention comprises a safety helmet or hardhat 11, an outer shell member 20 having overall dimensions greater than hardhat 11 and spaced from and overlying the hardhat, air filtering means 30 located in the space between the outer shell member 20 and hardhat 11, a protective face shield assembly 35 attached to and depending from the front of outer shell member 20, a transparent face shield 60 mounted in the face shield assembly 35, face sealing means 65 to seal against a user's face from the temple, down across the bottom of the chin and up to the temple and air circulating means 70 located in the rear portion of outer shell member 20.

Hardhat 11 comprises a rigid shell 12 of high density polyethylene having an inner surface 13 and an outer surface 14 of generally dome shaped configuration and is formed with a visor 15 at its front end. A head supporting harness 16 is removably fastened to the inner surface 13 of shell member 12. Head supporting harness 16 is made adjustable at the back to fit various head sizes.

Hardhat 11 is an approved safety helmet and may be worn alone where hardhat protection is mandated or desired. When respiratory protection is required, hardhat 11 may be mated to the remainder of the components and thus be used as a powered air respirator with hardhat protection. A particularly desirable additional benefit gained by utilizing a standard hardhat as the building block of a powered air respirator resides in the fact that the respirator may be worn by several persons. Interchangeability of hardhat 11 eliminates the hygiene and morale problems which may be encountered when more than one person uses an item of personal protective equipment. Further, since the hardhat is fitted to the user, the powered air respirator may be used immediately upon assembly of the hardhat to the outer shell member 20.

Another problem encountered with the type of powered air respirators exemplified by Bancroft U.S. Pat. No 3,963,021 or Lowe et al. U.S. Pat. No. 4,133,308 or Gorman U.S. Pat. No. 4,136,688 has been post-filtering contamination of the air by particles in the hair. This contamination can result when a respirator is worn after a user has been exposed to a dusty environment or even if the user suffers from an extreme dandruff condition. The powered air respirator of the present invention isolates the hair from the air flow through the use of hardhat 11. If hardhat 11 is contaminated due to having been worn in a dusty environment, it can easily be blown clean prior to being assembled to the remainder of the respirator.

It will be seen in FIGS. 1, 3 and 4 that hardhat 11 is provided with a downturned lip 17 around its peripheral edge for a purpose to be described hereinafter.

Outer shell member 20 comprises a generally dome shaped rigid shell 21 vacuum-formed from high impact polystyrene sheet 0.13 inch thick having an inner surface 23 and an outer surface 24 with a visor 22 at its front end and is dimensioned to be larger than the outer surface 14 of rigid shell 12 of hardhat 11, as clearly shown in the drawings. In the assembled condition, rigid shell 21 is superposed over rigid shell 12 so that their side peripheries are in juxtaposition, i.e., downturned lip 17 of rigid shell 12 and side edge 25 of rigid shell 21 are juxtaposed. In order to seal the junction between the two shells against leakage of air, a strip 26 of resilient material such as a foam tape is applied along the inner surface 23 of each side edge 25 of rigid shell 21.

Figure 4:
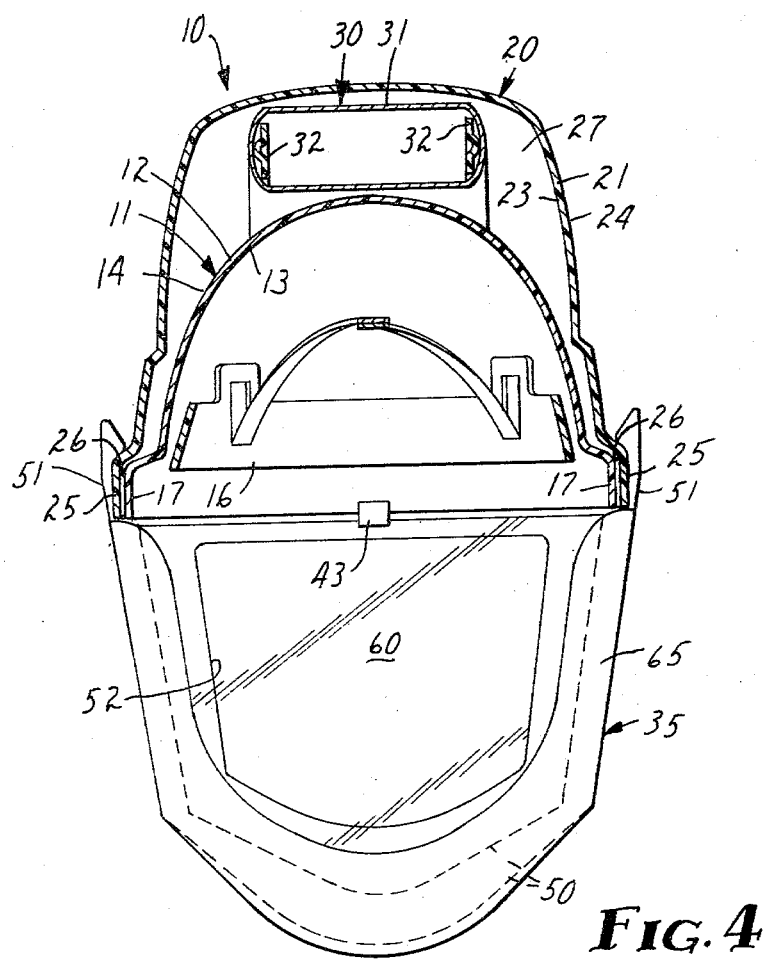
FIG. 4 is a sectional view along the line 4—4 of FIG. 2.

As shown in FIGS. 1, 3, and 4, the inner surface 23 of outer shell member 20 is spaced from the outer surface 14 of hardhat 11 when the two members are in superposed position thus forming a generally dome shaped passageway 27 extending between the front portion and the rear portion of the assembled shells. A slotted opening 28 for the passageway 27 is provided between the visor portion 15 of outer surface 14 of hardhat 11 and the visor portion 22 of inner surface 23 of outer shell member 20, across the entire frontal area.

In the embodiment of the invention illustrated in the drawings, air filtering means 30, in the form of a bag filter 31 is positioned in passageway 27. Filter 31 is typically a non-woven web of polymeric material having good filtering efficiency and low pressure drop characteristics. Where it is desired to protect a user in atmospheres contaminated with toxic dusts, mists or fumes, filters specially fabricated to remove such contaminants are utilized. Filters loaded with sorbent materials for removing hazardous materials from ambient air can also be used in those atmospheres. A filter support member 32 of generally rectangular shape with a tapered front end provides the necessary support for the bag filter 31 to maintain said bag filter in an "open" condition. The filter support member 32 is constructed of a tough lightweight plastic material such as high impact polystyrene. Bag filter 31 is slipped over support member 32 and is fastened in place by a filter strap 33 which fits around the base of the bag filter 31 and the underlying support member 32. A particularly useful fastening means for the ends of filter strap 33 are "hook and loop" strips applied to each end of the strap. Other fastening means such as a buckle are equally useful and are contemplated.

Protective face shield assembly 35 is attached to the visor 22 of outer shell member 20 by hinge assembly 36. Hinge assembly 36 is fabricated from a tough, flex-resistant plastic material such as polypropylene. Hinge assembly 36 is formed in three segments, attachment plate 37 which is secured to visor 22 by bolts or rivets 38, a hinge portion 39 joined to and of thinner cross section then attachment plate 37 or attachment plate 40 which is secured to face shield assembly 35 with bolts or rivets 41. Underlying visor 22 and through which the bolts or rivets holding attachment plate 37 in place are secured is metal (0.06 inch aluminum) backup plate 42. Hook 43 depends at an angle of about 45° from the central front edge of backup plate 42 and engages the edge of downturned lip 17 of visor 15. A generally U-shaped metal (0.06 inch aluminum) backup plate 44 also underlies attachment plate 40. Tabs 45, 45 formed at each end of backup plate 44 are secured to frame 50 by bolts or rivets 46.

Latch 47 in the form a a pair of upstanding posts 48, 48 with an inwardly facing boss in the free end of each post is centrally located on attachment plate 37 and a complementary post 49 with an enlarged knobbed end for retention by the bosses on posts 48 is centrally located on attachment plate 40. Latch 47 will hold face shield assembly 35 in the raised portion shown in dotted lines in FIG. 1. While one form of latch has been described, other equally simple latching means are suitable and are contemplated.

Face shield assembly 35, vacuum-formed from high impact polystyrene sheet 0.13 inch thick, includes a frame 50 of generally U-shaped configuration in the Y-direction and extends down the sides of the user's face from a point just slightly below the temple and across the bottom of the chin. The bottom portion (below the chin) of the frame 50 is angled downwardly and outwardly to allow full mobility for the user. Hooks, 51, 51 are provided at the top edge of each side of frame 50 to hold face shield assembly 35 in the position shown in FIG. 1. Frame 50 is also of generally U-shaped configuration in the X-direction thus being gently bowed out in front of the user's face. Aperture 52 is provided in frame 50 and is sufficiently large to provide for substantially unobstructed forward and peripheral field of view for the user. Channels 53, 53 are provided along the longitudinal edges of aperture 52 into which the transparent face shield 60 is slid into place. Detents 54, 54 are provided at the top of each channel 53 to hold transparent face shield 60 in place.

Transparent face shield 60 is made of a tough flexible plastic material suitably die cut to size. A particularly useful material for face shield 60 is cellulose acetate having a thickness of 0.06 inch.

Face sealing means 65 in the form of a U-shaped gasket formed of a resilient material such as a foam is suitably fastened, such as with an adhesive, along the peripheral edge of frame 50 so as to seal the face shield assembly 35 along the sides and across the chin of the user's face to seal off outside air from entering the face area. Since face sealing means 65 does not extend above the temples of the user, air exit areas are provided at each temple.

Air circulating means 70 comprises a motor fan assembly 71 of the impeller type well known to those skilled in the art. The motor fan assembly 71 has a rated output of 6 to 15 cfm of air and is powered by four rechargeable nickel-cadmium D-cells (not shown) with a total power output of 4.0 ampere hours at a nominal voltage of 4.8 volts. Motor fan assembly 71 is connected to the batteries by cord 72 which is fitted with a polarized plug (not shown). The plug functions as an on-off switch for the motor fan assembly 71. The batteries are fitted into a waist belt worn by the user. It has been found that air flows of about 6.5 cfm provide adequate fresh filtered air past the user's face and effectively prevents infiltration of ambient air into the respirator. Since all of the air is directed downwardly over the user's face due to the enclosed double shell plenum arrangement of the present invention, there is an "apparent" air flow which is far greater than the actual air flow.

Motor fan assembly 71 is mounted into a motor and filter support mounting assembly, generally designated by the reference numeral 73. One end of the mounting assembly 73 is connected to the filter support member 32 and communicates with the interior of bag filter 31. The other end of mounting assembly 73 is fastened to a flange 74 of generally lunate shape which fits over the rear peripheral edge of outer shell member 20 and the rear peripheral edge of downturned lip 17 of hardhat 11 to close the rear opening of the passageway 27. If desired, flange 74 could be formed as an integral part of mounting assembly 73.

A foraminous cover member 75 fits over the air intake manifold of motor fan assembly 71 and is removably attached by quarter-turn screws or other releasable fasteners (not shown) passing through flange 74 into retainers (not shown) secured on the inner surface 23 of outer shell 20. If desired, a prefilter (not shown) for filtering out large particulate matter can be fitted under cover member 75.

While the powered air respirator has been described as a self-contained battery powered unit, it will be apparent that the principles of the invention are generally applicable to a supplied air respirator. In the event that the supplied air is prefiltered, the entire air circulating means 70 and air filtering means 30 may be deleted. Cover member 75 would be modified to take the form of a plate bearing a coupling for a supplied air hose.

It will be noted that a flat area 77 has been provided at the front of outer shell member 20 to make it possible to mount a miner's lamp (not shown) on said flat area if added illumination is desired. Since it may be desirable to provide additional support for keeping the powered air respirator on a user's head, especially where the task being performed requires the user to bend forward, provision has been made in the hardhat for the use of a chin strap in the form of an upstanding lug (not shown) with an aperture therethrough on either side of the inner surface 13 immediately adjacent and above downturned lip 17. The chin strap is provided with a single hook fastener on each end thereof.

What is claimed is:

1. A powered air respirator providing hardhat, respiratory, eye and face protection comprising a hardhat, a shell member secured to said hardhat and spaced therefrom to form a generally dome shaped passageway therebetween, a face shield assembly attached to and depending from the front of said shell member having a peripheral edge which extends down the sides of the user's face from a point just slightly below the temples and across the bottom of the chin, a transparent face shield in said face shield assembly, face sealing means on the peripheral edge of said face shield assembly and terminating adjacent each temple of the user, to seal against a user's face from temple to temple, the terminal ends of said face sealing means being spaced from said shell member to define air exists from each side of said face shield assembly adjacent the temples of the user, and means for providing filtered air through said dome shaped passageway in a stream over the user's face and through said air exits above the user's temples.

2. A powered air respirator according to claim 1 wherein said means for providing filtered air comprises a bag form filter in said dome shaped passageway and an air circulating fan located in the space between said hardhat and said shell member.

3. A powered air respirator according to claim 1 wherein said means for providing filtered air comprises a central air supply source of filtered air connected to said respirator through an air line.

4. A powered air respirator according to claim 1 wherein the face shield assembly is hingeably attached to said shell member.

5. A powered air respirator comprising a hardhat having inner and outer surfaces, said hardhat having a lower open portion for receiving a user's head; supporting harness means located within the hardhat for supporting the hardhat on and spacing the inner surface thereof from the user's head; an outer shell member having inner and outer surfaces overlying the outer surface of said hardhat, said shell member and said hardhat being sealingly connected to each other along the superposed side peripheries and being otherwise in spaced relation defining between the outer surface of said hardhat and the inner surface of said shell member a domed longitudinal passageway extending between the front portion and rear portion of said shell member and having a slotted front opening formed between the outer surface of said hardhat and the inner surface of said shell member; filter means in said passageway extending substantially the full length thereof; a protective face shield assembly attached to and depending from the front edge of said outer shell member, said protective face shield assembly including a frame which extends down the sides of the user's face from a point just slightly below the temples and across the bottom of the chin; a transparent face shield fitted within the frame; face sealing means disposed along the peripheral edge of the frame and terminating adjacent each temple of the user to sealingly engage the user's face from temple to temple, the terminal ends of said face sealing means being spaced from said shell member to define air exits from each side of said face shield assembly adjacent the temples of the user and air circulating means mounted on a flange which sealingly engages the outer shell member to close the rear opening of said longitudinal passageway, said air circulating means extending into the space between the outer surface of said hardhat and the inner surface of said outer shell member and being connected to said filter means for directing air through said filter means, along the passageway forwardly of the outer surface of said hardhat, through the slotted front opening, downwardly across the face of the user and through said air exists at the user's temples.

6. A powered air respirator according to claim 5 wherein the face shield assembly is hingeably attached to said outer shell member.

* * * * *

UNITED STATES PATENT AND TRADEMARK OFFICE
CERTIFICATE OF CORRECTION

PATENT NO. : 4,280,491

DATED : July 28, 1981

INVENTOR(S) : Richard C. Berg and Emil J. Kvaal

It is certified that error appears in the above—identified patent and that said Letters Patent is hereby corrected as shown below:

Heading [75], "Kvall" should read -- Kvaal --;

Column 5, line 35, delete "," before "to";

Column 5, line 38, "exists" should read -- exits --;

Column 6, line 36, after "user" insert -- ; --;

Column 6, line 46, "exists" should read -- exits --.

Signed and Sealed this

Twenty-sixth Day of January 1982

[SEAL]

Attest:

Attesting Officer

GERALD J. MOSSINGHOFF

Commissioner of Patents and Trademarks